US00PP17091P3

(12) United States Plant Patent
Ui et al.

(10) Patent No.: US PP17,091 P3
(45) Date of Patent: Sep. 12, 2006

(54) ***CALIBRACHOA* PLANT NAMED 'KAKEGAWA S81'**

(50) Latin Name: ***Calibrachoa* sp.**
Varietal Denomination: Kakegawa S81

(75) Inventors: Akinobu Ui, Iwata (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 164 days.

(21) Appl. No.: 11/052,126

(22) Filed: Feb. 7, 2005

(65) Prior Publication Data

US 2006/0179528 P1 Aug. 10, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Jondle & Associates P.C.

(57) ABSTRACT

'Kakegawa S81' is a new *Calibrachoa* cultivar particularly distinguished by having a deep rose flower color, a white corolla throat color and a semi-creeping growth habit.

1 Drawing Sheet

Figure 1:
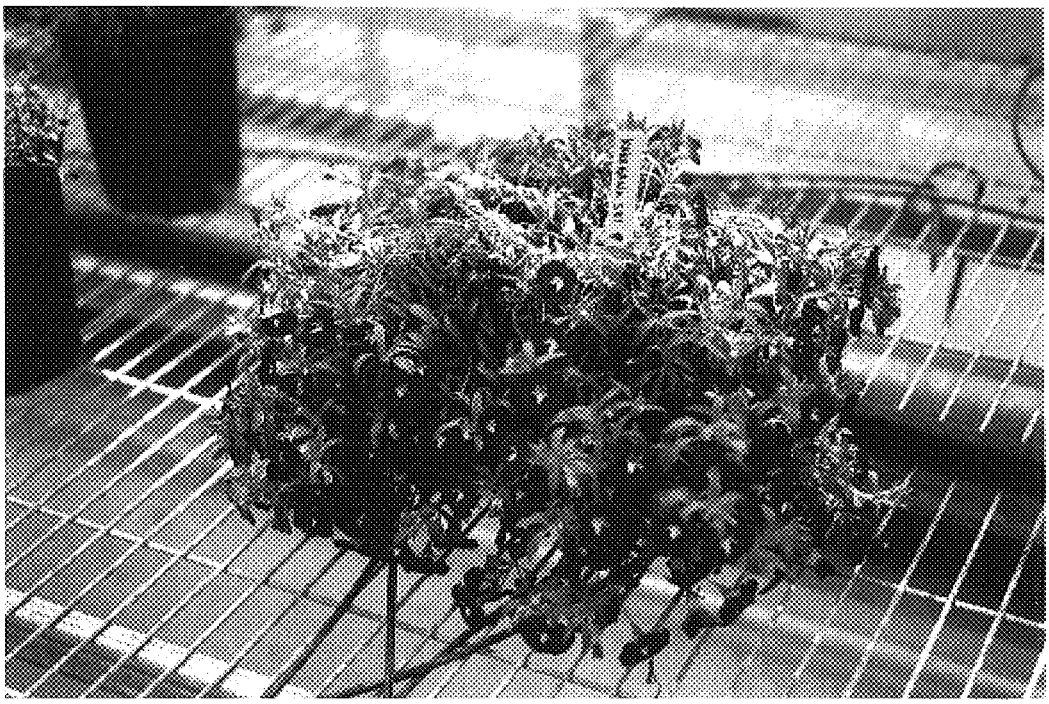

Genus and species: *Calibrachoa* sp.
Variety denomination: 'Kakegawa S81'.

BACKGROUND OF THE INVENTION

The present invention comprises a new and distinct cultivar of *Calibrachoa*, botanically known as *Calibrachoa* sp., and hereinafter referred to by the cultivar name 'Kakegawa S81'. It is characterized by having a rose flower color, a white corolla throat color and a semi-creeping growth habit. The new cultivar originated from a hybridization made in Kakegawa, Japan in 1998. A proprietary *Calibrachoa* breeding line with white flowers and a creeping growth habit (female) was crossed with a proprietary *Calibrachoa* breeding line with rose flower color and a semi-creeping growth habit (male).

In February 1999, $F_1$ seed from the above hybridization was sown in the greenhouse. Four single-plant selections were made based on their purple-pink flower color and semi-creeping growth habit and intercrossed to produce $F_2$ seed. In August 1999, $F_2$ seed was sown and 120 total plants were evaluated. One single-plant selection was made based on its deep rose flower color and semi-creeping growth habit and asexually propagated through rooted plant cuttings in both Kakegawa, Japan and Salinas, Calif. 'Kakegawa S81' has been shown to reproduce true to type in successive generations of asexual propagation.

DESCRIPTION OF THE GENUS *CALIBRACHOA* LLAVE & LEX

The genus *Petunia* was originally established in 1803 by A. L. Jussieu, who described both *P. parviflora* and *P. nyctaginiflora* as type species. Using a non-horticultural system that selected the first mentioned species as the type species (lecotype), N. L. Britton and H. A. Brown declared *P. parviflora* as the type species for *Petunia* in 1913.

During the 1980'sand 1990, H. J. Wijsman published a series of articles regarding the ancestry of *P. hybrida*, the Garden *Petunia,* and the inter-relationship of several species classified as *Petunia*. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the *Petunia* genus, Wijsman and J. H. de Jong proposed transferring the 14 chromosome species to the genus *Stimoryne*. Horticulturists opposed reclassifying the Garden *Petunia* and in 1986, Wijsman proposed the alternative of making *P. nyctaginflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa*, originally established by Llave and Lexarza in 1825. *Calibrachoa parviflora* (= *C. mexicana* Llave & Lexarza) is now the type species for the genus *Calibrachoa*.

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

FIG. 1. shows overall plant habit.

Figure 2:
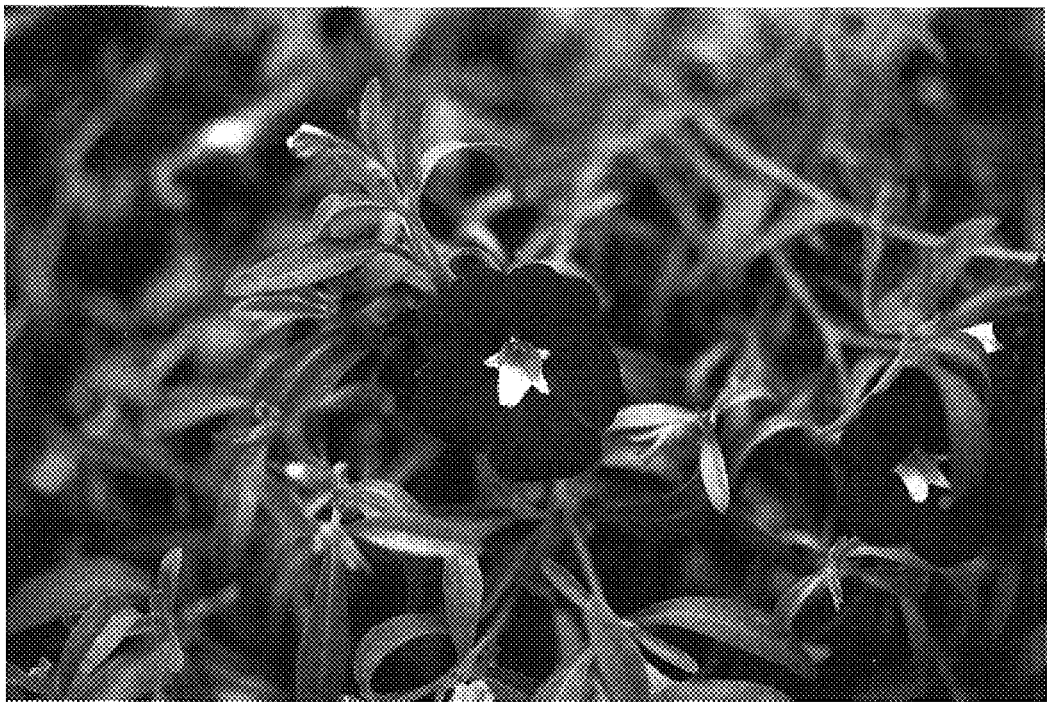

FIG. 2. shows the mature flower.

DESCRIPTION OF THE NEW CULTIVAR

The following detailed description sets forth the distinctive characteristics of 'Kakegawa S81'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Species.*—*Calibrachoa* sp. Cultivar 'Kakegawa S81'.
- *Common name.*—*Calibra choa.*

Parentage:
- *Male.*—Unnamed and unknown proprietary *Calibrachoa* breeding line.
- *Female.*—Unnamed and unknown proprietary *Calibrachoa* breeding line.

Plant description:
- *Life cycle.*—Tender Perennial.
- *Form.*—Freely branching.
- *Habit.*—Decumbent.
- *Height.*—8 cm as measured from soil level to top of plant.
- *Spread.*—50 cm.

Propagation:
- *Type cuttings.*—Vegetative cuttings.
- *Time to produce a rooted cutting.*—5–6 weeks.
- *Time to bloom from propagation.*—10 weeks after root development.

Environmental conditions for plant growth: The terminal 1.0–1.5 inches of actively growing stems were excised and the base of each cutting dipped for one to two seconds in a 1:9 solution of DIP 'N GROW root inducing solution immediately prior to placing the cutting into a cell tray. The cell tray contained a moistened peat moss-based growing medium. The cuttings were misted with water from overhead for 10 seconds every 30 minutes until sufficient roots were formed. Rooted cuttings were transplanted and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C.

Stems:
- *Stem color.*—RHS 143C (green).
- *Anthocyanin color.*—77A (purple).
- *Pubescence.*—Present.
- *Pubescence color.*—*RHS* 155A (white).
- *Stem description.*—Ancipital (round).
- *Stem diameter.*—0.3 cm.
- *Stem length.*—1.8–2.0 cm from soil line to first node.
- *Internode length.*—2.0–3.0 cm.

Leaves:
- *Leaf arrangement.*—Opposite.
- *Leaf shape.*—Elliptical.
- *Leaf apex.*—Mucronate.
- *Leaf base.*—Decurrent.
- *Leaf margin.*—Entire.
- *Leaf surface.*—Rough, dull.
- *Leaf surface pubescence.*—Slight.
- *Pubscence color.*—*RHS* 155A (white).
- *Venation.*—Pinnate.
- *Leaf length.*—2.5–3.5 cm.
- *Leaf width.*—0.6–0.9 cm.
- *Leaf color.*—Upper surface: RHS 137B (green). Lower surface: RHS 138A (green).
- *Petiole length.*—0.3–0.5 cm.
- *Petiole color.*—*RHS* 144A (yellow-green).

Inflorescence:
- *Flowering habit.*—Indeterminate.
- *Flower type.*—Solitary.
- *Flowering requirements.*—Will flower so long as day length is greater than 12 hours and temperature exceeds 13° C.
- *Duration of flowers.*—About 5 days.
- *Corolla shape.*—Flowers are funnel-shaped with five fused petals and five fissures dividing the petals and a shallow, yet prominent, indentation of the petal tip at the midvein.
- *Fragrance.*—Absent.

Flower buds:
- *Bud surface.*—Pubescent.
- *Bud length.*—1.2–1.5 cm.
- *Bud diameter.*—0.3–0.5 cm.
- *Bud shape.*—Ovate.
- *Bud color.*—RHS 4B (yellow) with RHS 77A (purple) stripes.
- *Peduncle length.*—1.1–1.5 cm.
- *Peduncle color.*—*RHS* 144B (yellow-green).

Flower description:
- *Flower depth.*—2.3–2.7 cm.
- *Flower tube length.*—1.2–1.5 cm.
- *Flower tube diameter.*—0.5 cm.
- *Flower diameter.*—2.5–3.5 cm.
- *Calyx.*—5 sepals, free.
- *Sepals.*—Shape: Lanceolate. Apex: Mucronate. Margin: Entire. Sepal color: Upper surface: 137A (green) at tip fading to RHS 141C (green) at base. Lower surface: 141B (green).
- *Petal shape.*—Spatulate.
- *Petal length.*—1.3 cm.
- *Petal width.*—1.6 cm.
- *Petal apex.*—Retuse (notched).
- *Petal margin.*—Entire.
- *Petal texture.*—Glabrous.
- *Petal color.*—Lobe color: Upper surface: RHS 74A (red-purple) with RHS 77A (purple) midvein. Lower surface: RHS 81C (purple-violet) with a RHS 77A (purple) midvein. Corolla tube color: Inner: RHS 5B (yellow) with RHS 77A (purple) midvein and a RHS 155A (white) triangular patch between the petal throat and petal lobe. Outer: RHS 160C (gray-yellow) with RHS 77A (purple) veins.

Reproductive organs:
- *Stamen number.*—5, free.
- *Stamen color.*—RHS 144C (yellow-green).
- *Pollen color.*—RHS 5B (yellow).
- *Ovary.*—Superior.

*Pistil number.*—1 per inflorescence.
*Pistil length.*—0.89 mm.
*Stigma color.*—RHS 144A (yellow-green).
*Style length.*—0.69 mm.
*Style color.*—*RHS* 144A (yellow-green).

Disease and insect resistance: 'Kakegawa S81' has excellent resistance to rain, heat and drought, although it will not tolerate temperature below 10° C. 'Kakegawa S81' is susceptible to *Botrytis*, powdery mildew, various stem and root rots, and certain viruses, such as Tobacco Mosaic Virus and *Impatiens* Necrotic Spotted Virus. 'Kakegawa S81' is also susceptible to aphids, leafminers, whiteflies and various *Lepidoptera*.

Comparison with Known Cultivars

*Calibrachoa* 'Kakegawa S81' is a distinct variety of *Calibrachoa* due to its rose flower color and white corolla throat color. 'Kakegawa S81' is distinguished from known cultivars mainly by flower color as shown in Table 1 below.

TABLE 1

| Characteristic | 'Kakegawa S81' | '982-1' | 'K7-1158' |
|---|---|---|---|
| Flower color | Deep Rose | White | Rose |

'Kakegawa S81' is most similar to the variety 'Kakegawa S54' (U.S. Plant Pat. No. 14,840); however, there are differences in flower petal color and corolla tube color as described in Table 2 below.

TABLE 2

| Characteristic | 'Kakegawa S81' | 'Kakegawa S54' |
|---|---|---|
| Petal color, upper surface | RHS 74A (red-purple) with RHS 77A (purple) midvein | RHS 48C (red) with RHS 47A (red) midvein |
| Petal color, lower surface | RHS 81C (purple-violet) with RHS 77A (purple) midvein | RHS 50A (red) |
| Outer corolla tube color | RHS 160C (gray-yellow) with RHS 77A (purple) veins | RHS 6A (yellow) |

We claim:

1. A new and distinct cultivar of *Calibrachoa* plant as shown and described herein.

* * * * *